(12) United States Patent
Ross et al.

(10) Patent No.: US 8,915,154 B2
(45) Date of Patent: Dec. 23, 2014

(54) SYSTEM AND METHOD FOR PREPARATION OF A SAMPLE

(75) Inventors: Kenneth J. Ross, Des Moines, IA (US);
Keith J. Quanbeck, Ankeny, IA (US);
Gang Wan, Grimes, IA (US); Jeffrey D. Wille, Ankeny, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 262 days.

(21) Appl. No.: 13/561,972

(22) Filed: Jul. 30, 2012

(65) Prior Publication Data

US 2013/0025380 A1 Jan. 31, 2013

Related U.S. Application Data

(60) Provisional application No. 61/513,293, filed on Jul. 29, 2011.

(51) Int. Cl.
*G01N 1/28* (2006.01)
(52) U.S. Cl.
CPC ........ *G01N 1/286* (2013.01); *G01N 2001/2866* (2013.01)
USPC ...................................... 73/864.91
(58) Field of Classification Search
CPC ...................................... G01N 1/286
See application file for complete search history.

(56) References Cited

U.S. PATENT DOCUMENTS

| | | |
|---|---|---|
| 3,310,292 A | 3/1967 | Moore |
| 3,556,731 A | 1/1971 | Martin |
| 3,736,614 A | 6/1973 | Crostic et al. |
| 3,789,670 A | 2/1974 | Rosenwald |
| 4,043,514 A | 8/1977 | Peterson, Jr. |
| 4,118,801 A | 10/1978 | Kraft et al. |
| 4,295,613 A | 10/1981 | Moore et al. |
| 4,413,059 A | 11/1983 | Tihon et al. |
| 4,534,858 A | 8/1985 | Aldrich et al. |
| 4,556,639 A | 12/1985 | Izawa et al. |
| 4,571,087 A | 2/1986 | Ranney |
| 4,747,693 A | 5/1988 | Kahl |
| 4,837,935 A | 6/1989 | Maier et al. |
| 4,883,644 A | 11/1989 | Perlman |
| 5,110,556 A | 5/1992 | Lyman et al. |
| 5,114,858 A | 5/1992 | Williams et al. |
| 5,153,136 A | 10/1992 | Vandenburgh |
| 5,183,564 A | 2/1993 | Hong |

(Continued)

FOREIGN PATENT DOCUMENTS

DE 29615162 12/1996

*Primary Examiner* — Paul West
(74) *Attorney, Agent, or Firm* — Pioneer Hi-Bred Int'l Inc.

(57) ABSTRACT

A system and method for the automated preparation of one or more samples for analysis is disclosed. The system comprises a processing mechanism configured to process the one or more samples, wherein each sample is contained in a separate sample container. The system further comprises a cover configured to enclose the sample containers while the processing mechanism is operating, a first holder comprising a first pivot point and a second pivot point, wherein the first pivot point of the first holder is hingedly connected to the cover, a second holder comprising a first pivot point and a second pivot point, wherein the first pivot point of the second holder is hingedly connected to the cover, a first actuator interface arm hingedly connected to the second pivot point of the first holder, and a second actuator interface arm hingedly connected to the second pivot point of the second holder.

9 Claims, 3 Drawing Sheets

(56) References Cited

U.S. PATENT DOCUMENTS

| | | |
|---|---|---|
| 5,272,092 A | 12/1993 | Hamasaki et al. |
| 5,458,416 A | 10/1995 | Edwards et al. |
| 5,464,773 A | 11/1995 | Melendez et al. |
| 5,501,521 A | 3/1996 | Hjalmarson |
| 5,707,861 A | 1/1998 | Sherman et al. |
| 5,921,477 A | 7/1999 | Tomes et al. |
| 2004/0071595 A1* | 4/2004 | Neeper et al. ............ 422/72 |

* cited by examiner

US 8,915,154 B2

SYSTEM AND METHOD FOR PREPARATION OF A SAMPLE

CROSS-REFERENCE TO RELATED APPLICATIONS

The present application claims priority from U.S. Provisional Application No. 61/513,293, filed Jul. 29, 2011, which is hereby incorporated herein by reference in its entirety. The disclosure of U.S. Pat. No. 5,921,477 is incorporated by reference.

FIELD OF THE INVENTION

Various embodiments of the present invention relate generally to systems and methods for preparation of a sample for analysis. More particularly, embodiments of the present invention provide systems and methods for preparing tissue for extracting material such as proteins, nucleic acids, starches, carbohydrates, oils, and the like.

BACKGROUND OF THE INVENTION

In scientific examination of plants and their cellular structures and components, it is often necessary to extract certain materials for close inspection, replication, experimentation, etc. These materials include nucleic acids, proteins, starches, carbohydrates, oils, and the like. In other disciplines, it is often necessary to grind, crush, or otherwise process materials in preparation for analysis. For example, it may be necessary to grind, crush, or otherwise process a solid material such as a rock or mineral to determine its chemical composition.

An apparatus for tissue preparation is disclosed in U.S. Pat. No. 5,921,477, ("the '477 patent"), the disclosure of which is incorporated by reference. In one embodiment of the invention of the '477 patent, an apparatus and method for preparing tissue samples for DNA, RNA or protein extraction includes a reciprocating saw mounted to a frame and connected to a plurality of tissue sample containers containing tissue samples and processing members. By activating the reciprocating saw, the tissue samples are ground by the processing members. Prior to activating the reciprocating saw, the tissue sample containers must be securely mounted to the frame.

Securing of sample containers to the frame is typically performed manually. To provide for high throughput extraction of various materials from the samples, there is a demand for automated systems and methods for preparing samples for analysis.

SUMMARY OF THE INVENTION

A system and method for the automated preparation of one or more samples for analysis is disclosed. In one embodiment, the samples comprise tissue samples being prepared for the extraction of materials therefrom. Alternatively, the samples may comprise any other material for which grinding of the material is a prerequisite for analysis. The system comprises a processing mechanism configured to grind, crush, or otherwise process the one or more samples, wherein each sample is contained in a separate sample container. The system further comprises a cover configured to enclose the sample containers while the processing mechanism is operating, a first holder comprising a first pivot point and a second pivot point, wherein the first pivot point of the first holder is hingedly connected to the cover, a second holder comprising a first pivot point and a second pivot point, wherein the first pivot point of the second holder is hingedly connected to the cover, a first actuator interface arm hingedly connected to the second pivot point of the first holder, and a second actuator interface arm hingedly connected to the second pivot point of the second holder.

DETAILED DESCRIPTION OF THE INVENTION

Figure 1:
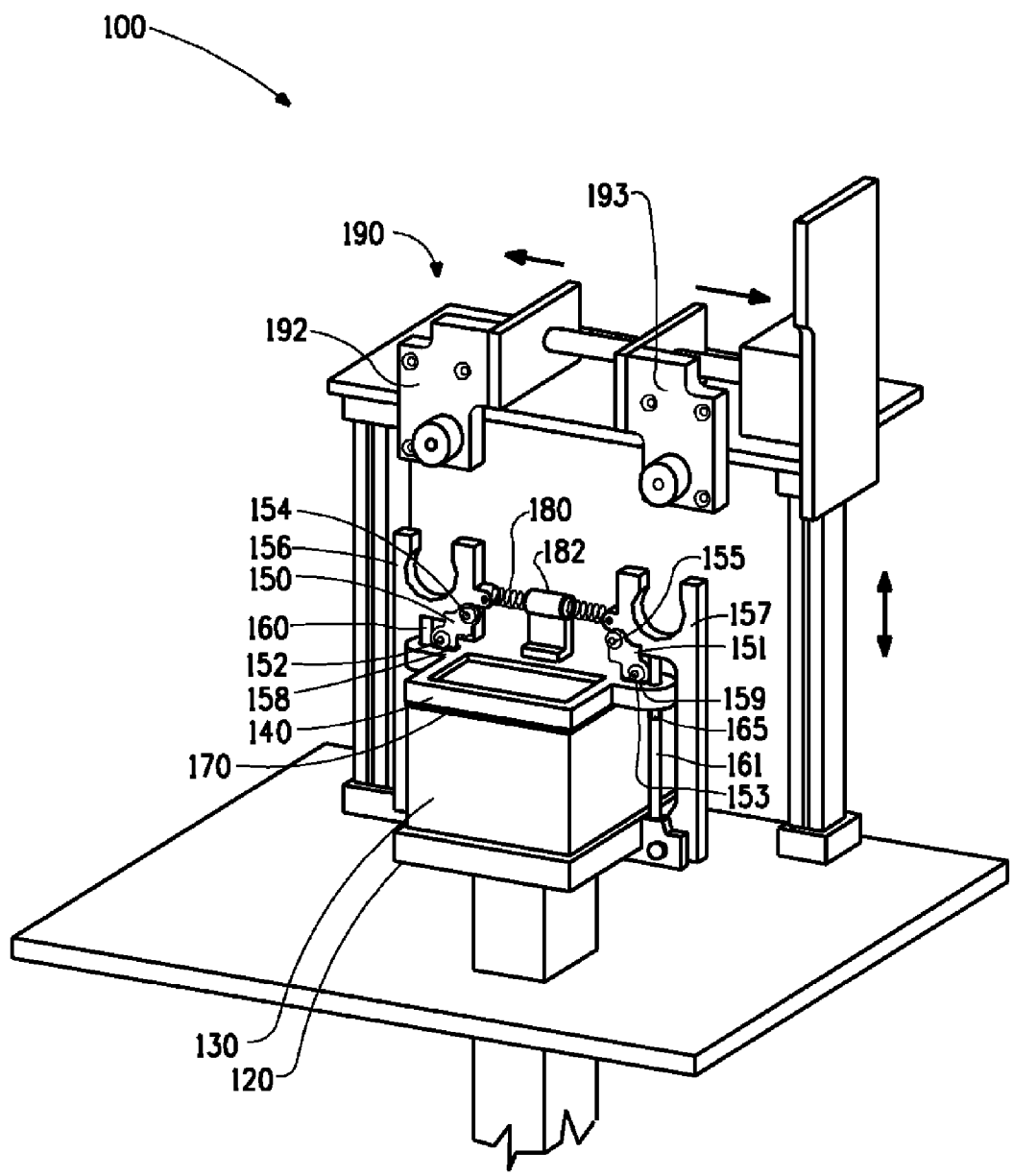
FIG. 1 illustrates an embodiment of a system for the automated preparation of one or more samples for analysis.

As shown in FIG. 1, in one embodiment, a system 100 for the automated preparation of one or more samples for analysis comprises a processing mechanism (not shown) configured to grind, crush, or otherwise process the one or more samples, wherein each sample is contained in a separate sample container 130, a cover 140 configured to enclose the sample containers 130 while the processing mechanism is operating, a first holder 150 comprising a first pivot point 152 and a second pivot point 154, and a second holder 151 comprising a first pivot point 153 and a second pivot point 155. The first pivot point 152 of first holder 150 is hingedly connected to the cover 140, and first actuator interface arm 156 is hingedly connected to the second pivot point 154 of first holder 150. The first pivot point 153 of second holder 151 is hingedly connected to the cover 140, and second actuator interface arm 157 is hingedly connected to the second pivot point 155 of second holder 151. The system 100 may further comprise a base 120 upon which the sample containers 130 rest while the processing mechanism is operating. The cover 140 may further comprise a first opening and a second opening, wherein the first opening is configured to surround a first guide rod 160, and the second opening is configured to surround a second guide rod 161. Guide rods 160 and 161 are substantially parallel to a direction of movement of the cover 140, and are configured to position the cover 140 relative to the sample containers 130. The system 100 may further comprise a seal 170 situated between the cover 140 and the sample containers 130. The system 100 may further comprise a control element (not shown) comprising hardware and software configured to control automatic operation of system 100. System 100 may further comprise an automated mechanism (not shown), such as a robotic arm, communicatively connected to the control element for automatically moving sample containers 130 in and out of system 100.

Processing Mechanism

System 100 comprises a processing mechanism configured to process samples in preparation for analysis. For example, in one embodiment, the processing mechanism may comprise the invention of U.S. Pat. No. 5,921,477, which relates to an apparatus and method for preparing tissue samples for DNA material extraction. These materials include nucleic acids, proteins, carbohydrates, starches, oils, and the like. A reciprocating saw is mounted to a frame and is connected to a plurality of containers holding tissue samples. The tissue sample containers each hold one or more processing members. When the reciprocating saw is activated, the plurality of containers agitate which causes the processing members to grind the tissue samples in preparation for material extraction. The apparatus may optionally include a hingable cover for covering the plurality of containers while they are agitated. A control panel may be connected to the apparatus for controlling the operation of the reciprocating saw.

While the processing mechanism of U.S. Pat. No. 5,921, 477 is described, the systems and methods of the present invention may be used in connection with any device capable of grinding, crushing, or otherwise reducing a sample to a form capable of being analyzed. Therefore, the processing mechanism may comprise another apparatus configured to prepare samples for extraction analysis.

Applicants have observed that a minimum stroke length (the distance travelled by the processing mechanism) of 55 to 75 percent of the height of sample containers 130 is necessary for processing efficiency. The actual minimum is dependent upon the mass of the processing members used. Use of a stroke length less than 55 percent of the height of sample containers 130 may result in excessive processing time, which in turn creates excessive heating. Excessive heating can be detrimental to the samples, for example if the samples are tissue samples.

Sample Containers

The purpose of sample containers 130 is to hold one or more samples that are being prepared for analysis. In one embodiment, the samples comprise tissue samples being prepared for the extraction of materials therefrom. Alternatively, the samples may comprise any other material for which grinding of the material is a prerequisite for analysis.

One or more samples are placed in sample containers 130 with one sample placed in a separate compartment of sample containers 130. In one embodiment, one or more processing members are also placed in each separate compartment of sample containers 130. The purpose of the processing members is to grind, crush, or otherwise process the samples. In one embodiment, the processing members comprise small copper or stainless steel balls, BBs, or ball bearings.

System 100 may comprise a base 120 that is securely mounted to the processing mechanism. The purpose of base 120 is to provide a stable platform upon which sample containers 130 are held while the processing mechanism is operating. Once the samples and processing members are placed in sample containers 130, sample containers 130 are placed on base 120 or directly upon the processing mechanism.

In one embodiment, sample containers 130 may comprise a standard 96 cell well plate. Alternatively, sample containers 130 may comprise another size well plate, sample tubes, or another type of enclosure capable of containing samples.

Cover

System 100 comprises a cover 140 configured to enclose the sample containers 130 while the processing mechanism is operating. Cover 140 is of a suitable size and shape to cover sample containers 130, and is configured to hold sample containers 130 securely when one or more actuator interface arms 156 and 157 are in the closed position.

In one embodiment, system 100 may comprise a seal 170. Seal 170 comprises a sheet comprising rubber or another elastomeric material, and is placed between sample containers 130 and cover 140. Seal 170 prevents sample material from escaping from sample containers 130 while the processing mechanism is operating. Seal 170 also further secures sample containers 130 when one or more actuator interface arms 156 and 157 are in the closed position.

Holders

System 100 comprises a first holder 150 and a second holder 151. In one embodiment, holders 150 and 151 are situated at opposite ends of cover 140. First holder 150 comprises a first pivot point 152, a second pivot point 154, and a presser 158. Second holder 151 comprises a first pivot point 153, a second pivot point 155, and a presser 159. Pressers 158 and 159 are configured to engage and secure cover 140. First pivot point 152 of first holder 150 is hingedly connected to cover 140, and first pivot point 153 of second holder 151 is hingedly connected to cover 140. Second pivot point 154 of first holder 150 is hingedly connected to first actuator interface arm 156. Second pivot point 155 of second holder 151 is hingedly connected to second actuator interface arm 157.

When actuator interface arms 156 and 157 are in the closed position, holders 150 and 151 apply force to cover 140 at pressers 158 and 159, causing cover 140 to be pressed securely against sample containers 130, and allowing sample containers 130 to be held securely when the processing mechanism is operating. When actuator interface arms 156 and 157 are in the open position, holders 150 and 151 lift cover 140 from sample containers 130, allowing sample containers 130 to be accessed.

Actuator Interface Arms

System 100 comprises a first actuator interface arm 156 and a second actuator interface arm 157. First actuator interface arm 156 is hingedly connected to second pivot point 154 of first holder 150. Second actuator interface arm 157 is hingedly connected to second pivot point 155 of second holder 151.

Figure 2:
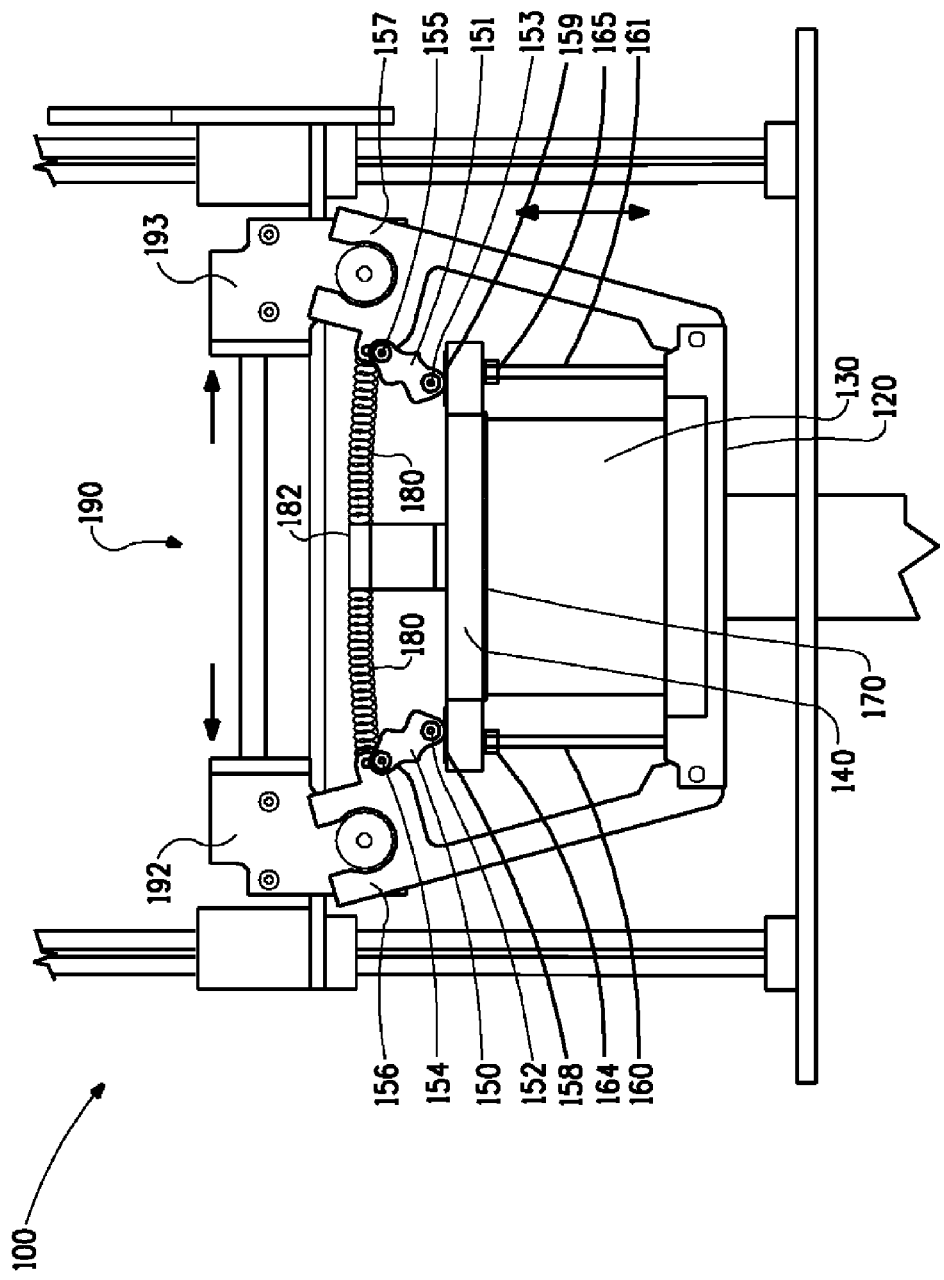
FIG. 2. further illustrates an embodiment of a system for the automated preparation of one or more samples for analysis.

First actuator interface arm 156 is configured to engage a first actuator arm 192, and second actuator interface arm 157 is configured to engage a second actuator arm 193. Actuator arms 192 and 193 are connected to actuator assembly 190. Actuator assembly 190 moves actuator arms 192 and 193 in a first direction to engage actuator interface arms 156 and 157, and in a second direction to move actuator interface arms 156 and 157 between open and closed positions. In one embodiment, actuator assembly 190 moves actuator arms 192 and 193 vertically and in a downward direction to engage actuator interface arms 156 and 157, and then moves actuator arms 192 and 193 horizontally and outwardly to move actuator interface arms 156 and 157 into the open position as shown in FIG. 2. Actuator assembly 190 moves actuator arms 192 and 193 horizontally and inwardly to place actuator interface arms 156 and 157 into the closed position as shown in FIG. 1, and then moves vertically and in an upward direction to place actuator arms 192 and 193 and actuator 190 out of the path of motion of the processing mechanism and other system 100 components when the processing mechanism is operating.

When actuator interface arms 156 and 157 are in the closed position, holders 150 and 151 apply force to cover 140 causing cover 140 to be pressed securely against sample containers 130, and allowing sample containers 130 to be held securely when the processing mechanism is operating. When actuator interface arms 156 and 157 are in the open position, holders 150 and 151 lift cover 140 from sample containers 130, allowing sample containers 130 to be accessed.

In one embodiment, a spring 180 may connect actuator interface arms 156 and 157. Spring 180 prevents actuator interface arms 156 and 157 from moving from the closed position to the open position when the processing mechanism is operating. A spring stabilizer 182 having a first end connected to spring 180 and a second end connected to cover 140 may be provided. The purpose of spring stabilizer 182 is to prevent vibration of spring 180 while the processing mechanism is operating.

Guide Rods

System 100 may comprise a first guide rod 160 and a second guide rod 161 for positioning cover 140 relative to sample containers 130. Guide rods 160 and 161 are substantially parallel to the direction of motion of cover 140. Cover 140 further comprises a first opening which surrounds first guide rod 160, and a second opening which surrounds second guide rod 161. Cover 140 may further comprise a first bushing 164 inserted into the first opening in cover 140 and further surrounding first guide rod 160. Cover 140 may further comprise a second bushing 165 inserted into the second opening in cover 140 and further surrounding second guide rod 161. The purpose of guide rods 160 and 161 is to position cover 140 relative to sample containers 130. As actuator interface arms 156 and 157 are moved into the open position, the openings in cover 140 or bushings 164 and 165 travel along guide rods 160 and 161 such that cover 140 moves away from sample containers 130 and in a direction that is substantially parallel to guide rods 160 and 161. As actuator interface arms 156 and 157 are moved into the closed position, the openings in cover 140 or bushings 164 and 165 travel along guide rods 160 and 161 such that cover 140 moves toward sample containers 130 and in a direction that is substantially parallel to guide rods 160 and 161. Thus, cover 140 does not experience rotation or translation while actuator interface arms 156 and 157 move between open and closed positions, and cover 140 returns to the proper position relative to sample containers 130 when actuator interface arms 156 and 157 move from the open to the closed position.

Base Height Compliance

It is important that cover 140 securely engage sample containers 130 to prevent sample material from escaping while the processing mechanism is operating. Therefore, base height compliance, or the distance from base 120 and cover 140, is an important consideration.

Seal 170 comprises a sheet comprising rubber or another elastomeric material, and is placed between sample containers 130 and cover 140. Seal 170 prevents sample material from escaping from sample containers 130 while the processing mechanism is operating. Seal 170 also is capable of expanding and contracting to ensure proper spacing between cover 140 and sample containers 130.

Alternatively, base height compliance may be achieved through the use of one or more springs. In one embodiment, to ensure that cover 140 securely engages sample containers 130, cover 140 may further comprise one or more springs (not shown) configured to press cover 140 securely against sample containers 130. As shown on page 11 of the Appendix, in another embodiment, to ensure that cover 140 securely engages sample containers 130, base 120 may comprise one or more springs configured to apply force upon base 120, causing sample containers 130 to be pressed securely against cover 140.

Application

Samples are placed in sample containers 130. Processing members may also be placed in sample containers 130 with the samples. In one embodiment, the samples comprise tissue samples being prepared for the extraction of materials therefrom. Alternatively, the samples may comprise any other material for which grinding of the material is a prerequisite for analysis.

Actuator assembly 190 moves actuator arms 192 and 193 in a first direction to engage actuator interface arms 156 and 157. In one embodiment, actuator assembly 190 moves actuator arms 192 and 193 vertically and in a downward direction to engage actuator interface arms 156 and 157. Actuator assembly 190 then moves actuator arms 192 and 193 in a second direction to move actuator interface arms 156 and 157 into an open position. In one embodiment, actuator assembly 190 moves actuator arms 192 and 193 horizontally and outwardly to move actuator interface arms 156 and 157 into the open position as shown in FIG. 2.

As actuator interface arms 156 and 157 move into the open position, first holder 150 rotates about the second pivot point 154 of first holder 150, and second holder 151 rotates about the second pivot point 155 of second holder 151. Additionally, first holder 150 rotates about the first pivot point 152 of first holder 150, and second holder 151 rotates about the first pivot point 153 of second holder 151. By the rotation of first holder 150 about the first pivot point 152 and the second pivot point 154 of first holder 150, first holder 150 is rotated such that the presser 158 of first holder 150 disengages from cover 140. Similarly, by the rotation of second holder 151 about the first pivot point 153 and the second pivot point 155 of second holder 151, second holder 151 is rotated such that the presser 159 of second holder 151 disengages from cover 140.

The combined motion of actuator interface arms 156 and 157 into the open position and the rotation of holders 150 and 151 cause cover 140 to be removed from sample containers 130. In one embodiment, cover 140 is lifted upward and away from sample containers 130.

Once cover 140 is removed from sample containers 130, sample containers 130 are removed from the processing mechanism or base 120 of the processing mechanism, and are replaced with other sample containers. In one embodiment, sample containers 130 are removed and replaced in an automated manner, e.g. by use of a robotic arm.

Once replacement sample containers 130 are in position, actuator assembly 190 moves actuator arms 192 and 193 in a second direction to engage actuator interface arms 156 and 157. In one embodiment, actuator assembly 190 moves actuator arms 192 and 193 horizontally to move actuator interface arms 156 and 157 into the closed position as shown in FIG. 1.

As actuator interface arms 156 and 157 move into the closed position, first holder 150 rotates about the second pivot point 154 of first holder 150, and second holder 151 rotates about the second pivot point 155 of second holder 151. Additionally, first holder 150 rotates about the first pivot point 152 of first holder 150, and second holder 151 rotates about the first pivot point 153 of second holder 151. By the rotation of first holder 150 about the first pivot point 152 and the second pivot point 154 of first holder 150, first holder 150 is rotated such that the presser 158 of first holder 150 engages cover 140. Similarly, by the rotation of second holder 151 about the first pivot point 153 and the second pivot point 155 of second holder 151, second holder 151 is rotated such that the presser 159 of second holder 151 engages cover 140.

The combined motion of actuator interface arms 156 and 157 into the closed position and the rotation of holders 150 and 151 cause cover 140 to be securely positioned relative to sample containers 130. In one embodiment, cover 140 is pushed downward and toward sample containers 130.

Once cover 140 is securely positioned relative to sample containers 130, actuator assembly 190 moves such that actuator assembly 190 and actuator arms 192 and 193 are removed from the path of motion of the processing mechanism and other system 100 components when the processing mechanism is operating. With cover 140 securely in position, removal of materials from the one or more samples can proceed by the operation of the processing mechanism.

Alternate Embodiment

Figure 3:
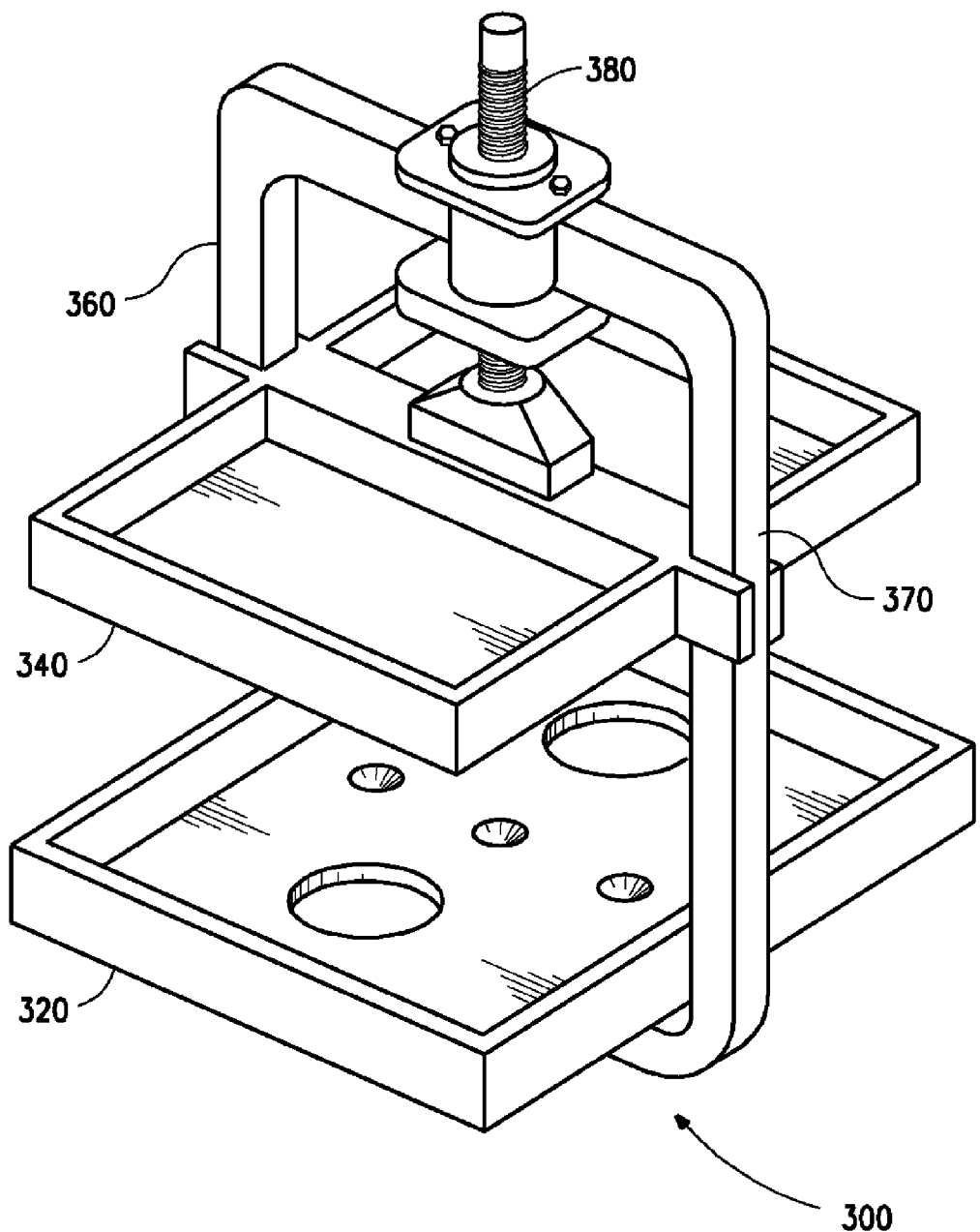
FIG. 3 illustrates another embodiment of a system for the automated preparation of one or more samples for analysis.

As shown in FIG. 3, in an alternate embodiment, a system 300 for the automated preparation of one or more samples for analysis comprises a processing mechanism (not shown) configured to grind, crush, or otherwise process the one or more samples, wherein each sample is contained in a separate sample container (not shown), a cover 340 configured to enclose the sample containers while the processing mechanism is operating, a base 320 upon which the sample containers rest while the processing mechanism is operating, a first guide rail 360 connected to a first end of base 320, a second guide rail 370 connected to a second end of base 320, and a screw 380 configured to move cover 340 relative to the sample containers. Guide rails 360 and 370 are substantially parallel to a direction of movement of the cover 340, and are configured to position the cover 340 relative to the sample containers. The system 300 may further comprise a seal (not shown) situated between the cover 340 and the sample containers. The system 300 may further comprise a control element (not shown) comprising hardware and software configured to control automatic operation of system 300. System 300 may further comprise an automated mechanism (not shown), such as a robotic arm, communicatively connected to the control element for automatically moving sample containers in and out of system 300. System 300 may optionally comprise an anti-backing off mechanism coupled to screw 380.

Samples are placed in sample containers. Processing members may also be placed in sample containers with the samples. An actuator assembly (not shown) rotates screw 380 in a first direction to cause cover 340 to be removed from the sample containers. For example, screw 380 may be rotated in a counterclockwise direction, causing cover 340 to be lifted upward and away from the sample containers.

Once cover 340 is removed from the sample containers, the sample containers may be removed from base 320, and may be replaced with other sample containers. In one embodiment, the sample containers are removed and replaced in an automated manner, e.g. by use of a robotic arm.

Once replacement sample containers are in position, the actuator assembly rotates screw 380 in a second direction to cause cover 340 to be moved onto the sample containers. For example, screw 380 may be rotated in a clockwise direction, causing cover 340 to be lowered onto the sample containers. The motion of screw 380 to place cover 340 onto the sample containers causes cover 340 to be securely positioned relative to the sample containers. In addition, cover 340 engages and travels along guide rails 360 and 370, preventing cover 340 from rotating or translating relative to the sample containers while cover 340 is in motion. With cover 340 securely in position, processing of the one or more samples in preparation for analysis can proceed by the operation of the processing mechanism.

System 300 may optionally comprise an anti-backing off mechanism coupled to screw 380. The purpose of the anti-backing off mechanism is to prevent rotation of screw 380 and subsequent movement of cover 340 relative to the sample containers during operation of the processing mechanism. The anti-backing off mechanism may comprise a spring washer or similar mechanism coupled to screw 380. In one embodiment, the anti-backing off mechanism surrounds screw 380. The actuator assembly contacts the anti-backing off mechanism as screw 380 is rotated by the actuator assembly to raise and lower cover 340. When lowering cover 340, anti-backing off mechanism may be freely rotated. When raising cover 340, a downward force is applied to the anti-backing off mechanism by the actuator assembly during rotation of screw 380, releasing the anti-backing off mechanism and allowing it to rotate as cover 340 is raised. In this embodiment, the operation of the anti-backing off mechanism is similar to that of a safety cap, for example those used on medicine containers. In another embodiment, the anti-backing off mechanism may comprise a clamp positioned on screw 380. By using the anti-backing off mechanism, screw 380 cannot rotate during operation of the processing mechanism; thus, cover 340 remains securely in position during operation of the processing mechanism.

Method

A method for the automated preparation of one or more samples for analysis comprises providing one or more samples and one or more sample containers, wherein each sample is contained in a separate sample container. In one embodiment, the samples comprise tissue samples being prepared for the extraction of materials therefrom. Alternatively, the samples may comprise any other material for which grinding of the material is a prerequisite for analysis. In one embodiment, each sample may be placed into a separate well of a standard well plate. One or more processing members may also be placed in each sample container to aid in grinding the sample. The method further comprises automatically securing the sample containers to a processing mechanism configured to grind, crush, or otherwise process the one or more samples. In one embodiment, the processing mechanism may comprise the system of U.S. Pat. No. 5,921,477. Alternatively, the processing mechanism may be any device capable of grinding, crushing, or otherwise processing the samples. The method further comprises processing the samples by the operation of the processing mechanism. The securing of the sample containers may be initiated and performed automatically, for example by a robotic arm. Processing may be initiated automatically by a controller. For example, the controller may comprise a general purpose computer or specialized hardware capable of running software for operating the processing mechanism, robotic arm, and other system components. The method may further comprise sealing the sample containers prior to processing the samples to prevent sample material from escaping from the sample containers while the system operates. Sealing may be accomplished by placing a cover onto the sample containers, or a seal may be placed between the sample containers and the cover.

While specific embodiments described herein pertain to tissue samples, the systems and methods may be applied to any material for which grinding, crushing, or otherwise processing is a prerequisite to further analysis.

Having described the preferred embodiment, it will become apparent that various modifications can be made without departing from the scope of the invention as defined in the accompanying claims.

The following is claimed:

1. A system for the automated preparation of one or more samples for analysis comprising:
    a processing mechanism configured to process the one or more samples, wherein each sample is contained in a separate sample container;

a cover configured to enclose the one or more sample containers while the processing mechanism is operating;

a first holder comprising a first pivot point and a second pivot point, wherein the first pivot point of the first holder is hingedly connected to the cover;

a second holder comprising a first pivot point and a second pivot point, wherein the first pivot point of the second holder is hingedly connected to the cover;

a first actuator interface arm hingedly connected to the second pivot point of the first holder; and a second actuator interface arm hingedly connected to the second pivot point of the second holder, wherein a first end of each actuator interface arm is hingedly connected to a base upon which the one or more sample containers rest while the processing mechanism is operating.

2. The system of claim 1 wherein the one or more samples comprise one or more tissue samples.

3. The system of claim 1 wherein the one or more sample containers comprise a well plate.

4. The system of claim 1 wherein each actuator interface arm further comprises a second end, and a protrusion.

5. The system of claim 4 wherein the second end of each actuator interface arm is configured to engage an actuator.

6. The system of claim 4 wherein the protrusion of the first actuator interface arm is hingedly connected to the second pivot point of the first holder and the second actuator interface arm is hingedly connected to the second pivot point of the second holder.

7. The system of claim 1 further comprising a seal situated between the cover and the one or more sample containers.

8. The system of claim 1 wherein a stroke length of the processing mechanism is at least 55 percent of a height of the one or more sample containers.

9. A system for the automated preparation of one or more samples for analysis comprising:

a processing mechanism configured to process the one or more samples, wherein each sample is contained in a separate sample container;

a cover configured to enclose the one or more sample containers while the processing mechanism is operating;

a first holder comprising a first pivot point and a second pivot point, wherein the first pivot point of the first holder is hingedly connected to the cover;

a second holder comprising a first pivot point and a second pivot point, wherein the first pivot point of the second holder is hingedly connected to the cover;

a first actuator interface arm hingedly connected to the second pivot point of the first holder; and a second actuator interface arm hingedly connected to the second pivot point of the second holder, wherein the cover further comprises a first opening and a second opening, the first opening in the cover surrounds a first guide rod, and the second opening in the cover surrounds a second guide rod, wherein the guide rods are substantially parallel to a direction of movement of the cover and are configured to position the cover relative to the one or more sample containers.

* * * * *